(12) United States Patent
Privitera et al.

(10) Patent No.: US 8,915,908 B2
(45) Date of Patent: Dec. 23, 2014

(54) CRYOGENIC PROBE

(75) Inventors: Salvatore Privitera, Mason, OH (US); Jeffrey T. Ruwe, Cincinnati, OH (US)

(73) Assignee: Atricure, Inc., West Chester, OH (US)

(*) Notice: Subject to any disclaimer, the term of this patent is extended or adjusted under 35 U.S.C. 154(b) by 1060 days.

(21) Appl. No.: 12/727,995

(22) Filed: Mar. 19, 2010

(65) Prior Publication Data

US 2010/0241114 A1    Sep. 23, 2010

Related U.S. Application Data

(60) Provisional application No. 61/161,993, filed on Mar. 20, 2009.

(51) Int. Cl.
*A61B 18/02* (2006.01)

(52) U.S. Cl.
CPC ......... *A61B 18/02* (2013.01); *A61B 2018/0287* (2013.01)
USPC .......................................................... 606/21

(58) Field of Classification Search
USPC .................................................... 606/20–26
See application file for complete search history.

(56) References Cited

U.S. PATENT DOCUMENTS

| | | | |
|---|---|---|---|
| 3,270,744 A | 9/1966 | Katz | |
| 3,272,203 A | 9/1966 | Chato | |
| 3,298,371 A | 1/1967 | Lee | |
| 3,391,690 A | 7/1968 | Armao | |
| 3,696,813 A * | 10/1972 | Wallach | 606/26 |
| 3,736,937 A | 6/1973 | Basiulis | |
| 3,859,986 A | 1/1975 | Okada | |
| 3,910,277 A | 10/1975 | Zimmer | |
| 4,018,227 A | 4/1977 | Wallach | |
| 4,082,096 A | 4/1978 | Benson | |
| 4,327,733 A | 5/1982 | Gallie | |

(Continued)

FOREIGN PATENT DOCUMENTS

WO    WO 03/061496 A1    7/2003

OTHER PUBLICATIONS

Allan C. Skanes, Raymond Yee, Andrew D. Krahn and George J. Klein, Cryoablation of Atrial Arrhythmias, Cardiac Electrophysiology Review 2002;6:383-388; 2002 Kluwer Academic Publishers. Manufactured in The Netherlands.

*Primary Examiner* — Michael Peffley
*Assistant Examiner* — Daniel Fowler
(74) *Attorney, Agent, or Firm* — Porter, Wright, Morris & Arthur LLP; Ryan L. Willis

(57) ABSTRACT

A cryogenic probe for ablating cardiac tissue is provided comprising a handle piece and an elongated probe tube extending from the handle that terminates in a malleable end effector closed at its distal end and having a smooth outer surface. A semi-rigid insulative sleeve extends from the handle and overlies the proximal portion of the probe tube. An internal support preferably in the form of a coiled spring is located interior of the probe tube for supporting the interior surface of the probe tube. A plurality of cryogenic fluid supply tubes are disposed on the interior of the probe tube for introducing cryogenic fluid to the probe tube, each supply tube having an outlet orifice, with the outlet orifices being staggered along the length of the probe tube. In one embodiment, the probe tube is axially movable relative to the sleeve/handle between retracted and extended positions. Also, the probe tube may be provided with a thermocouple for measuring the temperature of the surface of the probe tube.

16 Claims, 7 Drawing Sheets

(56) References Cited

U.S. PATENT DOCUMENTS

| | | | |
|---|---|---|---|
| 4,802,475 A | 2/1989 | Weshahy | |
| 5,078,713 A | 1/1992 | Varney | |
| 5,108,390 A | 4/1992 | Potocky | |
| 5,139,496 A | 8/1992 | Hed | |
| 5,147,355 A | 9/1992 | Friedman | |
| 5,254,116 A * | 10/1993 | Baust et al. | 606/23 |
| 5,275,595 A | 1/1994 | Dobak | |
| 5,281,215 A | 1/1994 | Milder | |
| 5,403,311 A * | 4/1995 | Abele et al. | 606/49 |
| 5,423,807 A | 6/1995 | Milder | |
| 5,571,088 A | 11/1996 | Lennox | |
| 5,571,159 A | 11/1996 | Alt | |
| 5,573,532 A * | 11/1996 | Chang et al. | 606/26 |
| 5,575,772 A | 11/1996 | Lennox | |
| 5,653,734 A | 8/1997 | Alt | |
| 5,713,942 A | 2/1998 | Stern | |
| 5,720,719 A | 2/1998 | Edwards | |
| 5,733,280 A | 3/1998 | Avitall | |
| 5,759,182 A | 6/1998 | Varney | |
| 5,797,960 A | 8/1998 | Stevens | |
| 5,800,487 A | 9/1998 | Mikus | |
| 5,823,956 A | 10/1998 | Roth | |
| 5,829,447 A | 11/1998 | Stevens | |
| 5,899,898 A | 5/1999 | Arless | |
| 5,899,899 A | 5/1999 | Arless | |
| 5,902,299 A | 5/1999 | Jayaraman | |
| 5,957,963 A | 9/1999 | Dobak | |
| 6,074,412 A | 6/2000 | Mikus | |
| 6,106,518 A | 8/2000 | Wittenberger | |
| 6,117,101 A | 9/2000 | Diederich | |
| 6,200,311 B1 * | 3/2001 | Danek et al. | 606/15 |
| 6,235,019 B1 | 5/2001 | Lehmann | |
| 6,241,722 B1 | 6/2001 | Dobak | |
| 6,270,476 B1 | 8/2001 | Santoianni | |
| 6,270,493 B1 | 8/2001 | Lalonde | |
| 6,283,959 B1 | 9/2001 | Lalonde | |
| 6,325,818 B1 | 12/2001 | Werneth | |
| 6,428,534 B1 | 8/2002 | Joye | |
| 6,450,948 B1 | 9/2002 | Matsuura | |
| 6,464,716 B1 | 10/2002 | Dobak | |
| 6,498,268 B1 | 12/2002 | Abboud | |
| 6,500,174 B1 | 12/2002 | Maguire | |
| 6,517,533 B1 | 2/2003 | Swaminathan | |
| 6,527,769 B2 | 3/2003 | Langberg | |
| 6,537,271 B1 | 3/2003 | Murray | |
| 6,540,740 B2 | 4/2003 | Lehmann | |
| 6,540,742 B1 | 4/2003 | Thomas | |
| 6,572,610 B2 | 6/2003 | Kovalcheck | |
| 6,575,966 B2 | 6/2003 | Lane | |
| 6,577,895 B1 | 6/2003 | Altman | |
| 6,579,287 B2 | 6/2003 | Wittenberger | |
| 6,592,577 B2 | 7/2003 | Abboud | |
| 6,595,988 B2 | 7/2003 | Wittenberger | |
| 6,602,247 B2 | 8/2003 | Lalonde | |
| 6,607,502 B1 | 8/2003 | Maguire | |
| 6,607,517 B1 | 8/2003 | Dae | |
| 6,607,545 B2 | 8/2003 | Kammerer | |
| 6,623,479 B1 | 9/2003 | Nun | |
| 6,629,972 B2 | 10/2003 | Lehmann | |
| 6,666,858 B2 | 12/2003 | Lafontaine | |
| 6,669,689 B2 | 12/2003 | Lehmann | |
| 6,679,268 B2 | 1/2004 | Stevens | |
| 6,685,732 B2 | 2/2004 | Kramer | |
| 6,723,092 B2 | 4/2004 | Brown | |
| 6,746,445 B2 | 6/2004 | Abboud | |
| 6,758,830 B1 | 7/2004 | Schaer | |
| 6,758,847 B2 | 7/2004 | Maguire | |
| 6,767,346 B2 | 7/2004 | Damasco | |
| 6,772,766 B2 | 8/2004 | Gallo | |
| 6,780,183 B2 | 8/2004 | Jimenez | |
| 6,796,979 B2 | 9/2004 | Lentz | |
| 6,869,431 B2 | 3/2005 | Maguire | |
| 6,887,234 B2 | 5/2005 | Abboud | |
| 6,893,433 B2 | 5/2005 | Lentz | |
| 6,899,709 B2 | 5/2005 | Lehmann | |
| 6,905,949 B2 | 6/2005 | Arita | |
| 6,913,604 B2 | 7/2005 | Mihalik | |
| 6,925,327 B2 | 8/2005 | Altman | |
| 6,926,711 B2 | 8/2005 | Lentz | |
| 6,936,045 B2 | 8/2005 | Yu | |
| 6,942,659 B2 | 9/2005 | Lehmann | |
| 6,955,175 B2 | 10/2005 | Stevens | |
| 6,974,416 B2 | 12/2005 | Booker | |
| 7,001,378 B2 | 2/2006 | Yon | |
| 7,013,169 B2 | 3/2006 | Bowe | |
| 7,022,105 B1 | 4/2006 | Edwards | |
| 7,037,290 B2 | 5/2006 | Gardeski | |
| 7,048,711 B2 | 5/2006 | Rosenman | |
| 7,060,062 B2 | 6/2006 | Joye | |
| 7,070,594 B2 | 7/2006 | Sherman | |
| 7,089,063 B2 | 8/2006 | Lesh | |
| 7,097,641 B1 | 8/2006 | Arless | |
| 7,099,717 B2 | 8/2006 | Woodard | |
| 7,100,614 B2 | 9/2006 | Stevens | |
| 7,101,362 B2 | 9/2006 | Vanney | |
| 7,101,368 B2 | 9/2006 | Lafontaine | |
| 7,118,565 B2 | 10/2006 | Abboud | |
| 7,137,395 B2 | 11/2006 | Fried | |
| 7,137,978 B2 | 11/2006 | Levin | |
| 7,156,816 B2 | 1/2007 | Schwartz | |
| 7,189,227 B2 | 3/2007 | Lafontaine | |
| 7,189,228 B2 | 3/2007 | Eum | |
| 7,195,625 B2 | 3/2007 | Lentz | |
| 7,207,986 B2 | 4/2007 | Abboud | |
| 7,218,958 B2 | 5/2007 | Rashidi | |
| 7,273,479 B2 | 9/2007 | Littrup | |
| 7,288,088 B2 | 10/2007 | Swanson | |
| 7,288,089 B2 | 10/2007 | Yon | |
| 7,291,142 B2 | 11/2007 | Eberl | |
| 7,291,143 B2 | 11/2007 | Swanson | |
| 7,291,144 B2 | 11/2007 | Dobak | |
| 7,300,433 B2 | 11/2007 | Lane | |
| 7,306,589 B2 | 12/2007 | Swanson | |
| 7,306,590 B2 | 12/2007 | Swanson | |
| 7,322,973 B2 | 1/2008 | Nahon | |
| 7,374,553 B2 | 5/2008 | Koerner | |
| 7,378,126 B2 | 5/2008 | Yamazaki | |
| 2003/0055415 A1 * | 3/2003 | Yu et al. | 606/21 |
| 2003/0212394 A1 * | 11/2003 | Pearson et al. | 606/41 |
| 2004/0073203 A1 | 4/2004 | Yu | |
| 2004/0243119 A1 | 12/2004 | Lane | |
| 2005/0010201 A1 | 1/2005 | Abboud | |
| 2005/0215946 A1 * | 9/2005 | Hansmann et al. | 604/66 |
| 2007/0021741 A1 | 1/2007 | Abboud | |
| 2007/0027444 A1 | 2/2007 | Levin | |
| 2007/0161974 A1 | 7/2007 | Abboud | |
| 2007/0167938 A1 | 7/2007 | Zvuloni | |
| 2007/0233055 A1 | 10/2007 | Abboud | |
| 2007/0299432 A1 | 12/2007 | Arless | |
| 2008/0045935 A1 | 2/2008 | Cox | |
| 2008/0103493 A1 | 5/2008 | Abboud | |
| 2008/0114345 A1 | 5/2008 | Arless | |

\* cited by examiner

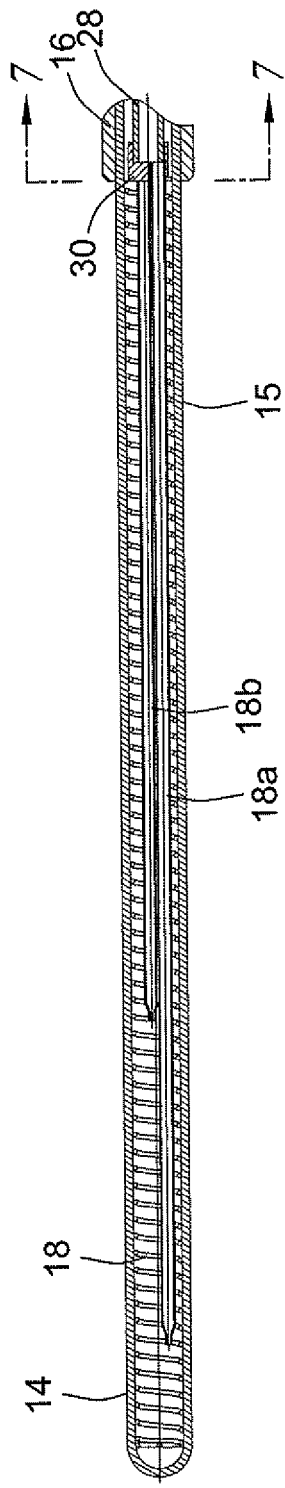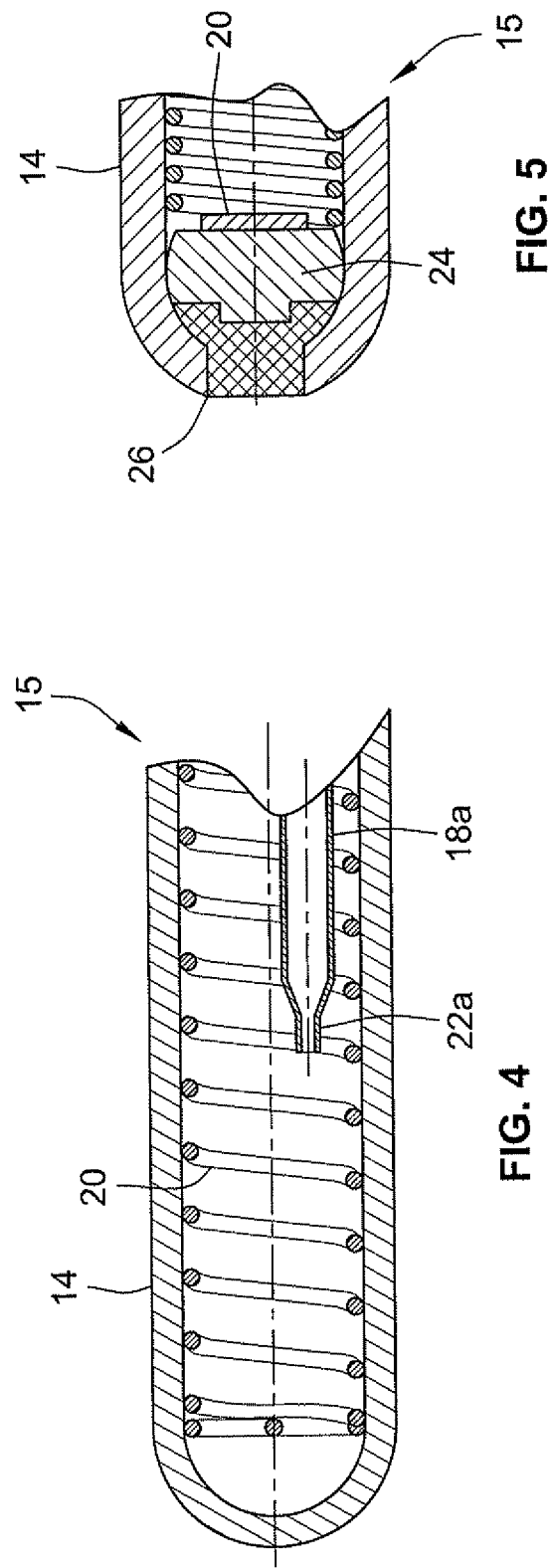
FIG. 3
FIG. 4
FIG. 5

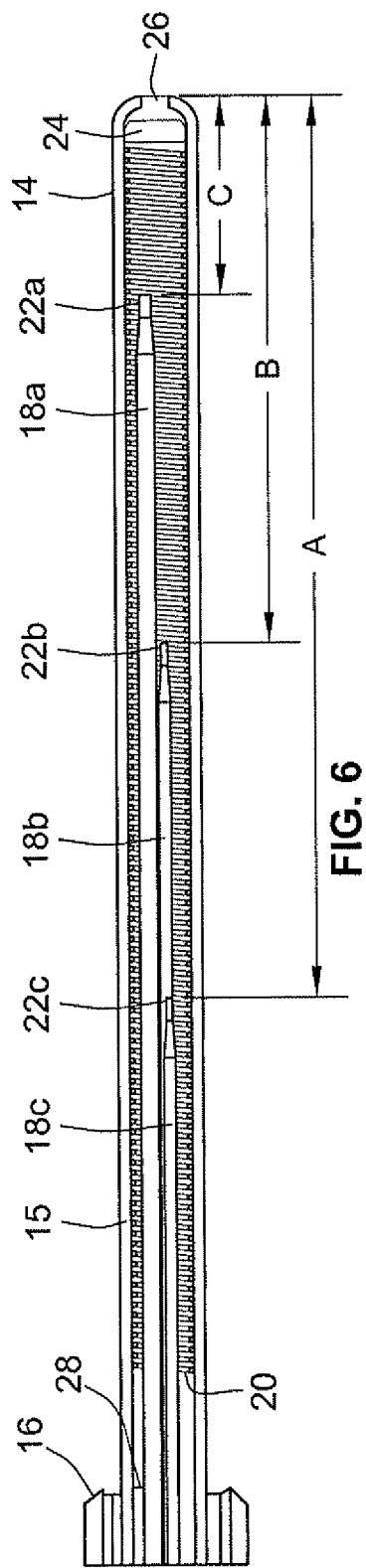
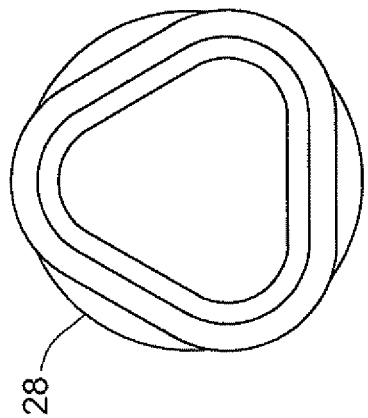
FIG. 8
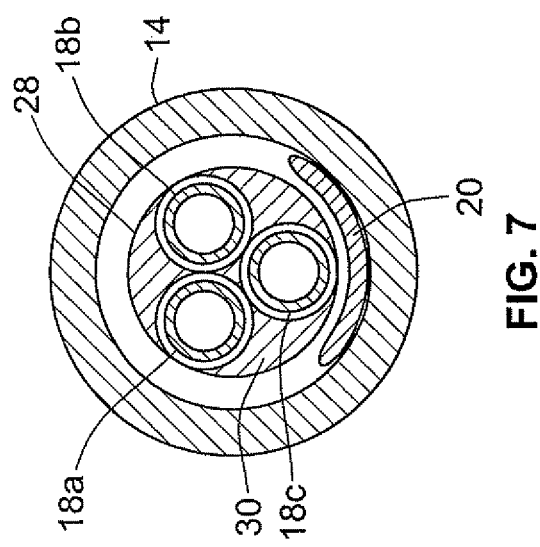
FIG. 7
FIG. 6

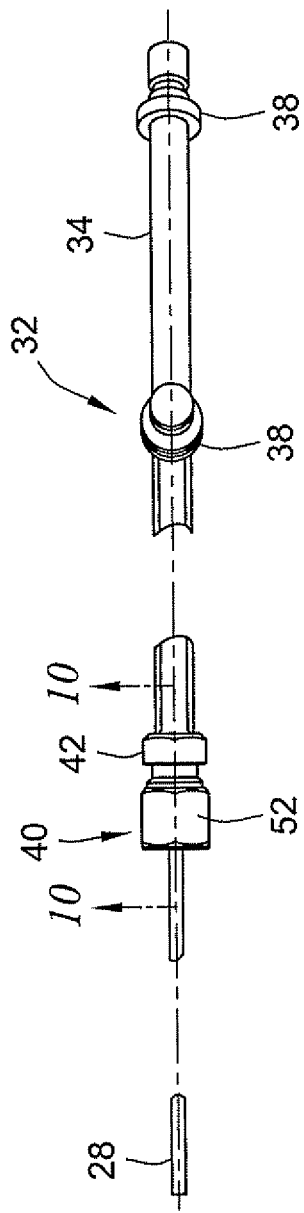
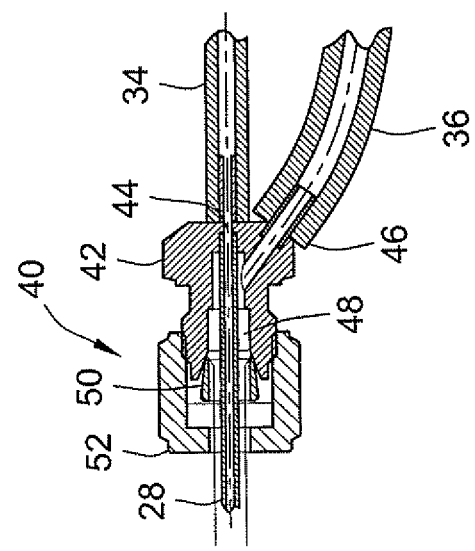
FIG. 9
FIG. 10

CRYOGENIC PROBE

CROSS REFERENCE TO RELATED APPLICATION

This application claims the benefit of the filing date of U.S. Provisional Application Ser. No. 61/161,993, filed Mar. 20, 2009, the entire contents of which are incorporated by reference herein.

BACKGROUND

It is known to treat cardiac arrhythmias by creating one or more lines of scar tissue or ablation in the heart tissue to block errant electrical signals. The present application is directed to a cryogenic surgical instrument and, more particularly, to a cryogenic probe or cryoprobe, for creating lines of ablation on cardiac tissue for the treatment of cardiac arrythmias, such as atrial fibrillation.

SUMMARY

In accordance with the present disclosure, a cryogenic probe for ablating cardiac tissue is provided that includes a hand piece, an elongated, insulative, semi-rigid sleeve extending from the hand piece, and a probe tube closed at its distal end and having a smooth outer surface that extends from the handle through the sleeve and terminates as a malleable end effector. The interior surface of the end effector includes additional support which, in an exemplary embodiment, is in the form of a coiled spring. A plurality of cryogenic fluid supply tubes is disposed on the interior of the probe tube for introducing cryogenic fluid. Each of the supply tubes has an outlet orifice for expansion of the cryogenic fluid, with the outlet orifices being staggered along the length of the end effector portion of the probe.

In keeping with one aspect of the disclosure, the probe may be retractable relative to the semi-rigid sleeve and handle so that the end effector may be protected from damage when not in use and to make the packaging more compact.

In another aspect, the probe may be provided with a thermocouple mounted on the exterior thereof for providing the user with a temperature reading for the tissue contacting portion of the end effector.

In an exemplary embodiment, the cryogenic fluid or cryofluid supply tubes are three in number and made from stainless steel. The orifice of each supply tube has a cross-sectional area (measured from the inside diameter) from about 0.00000707 sq. in. to about 0.0000785 sq. in. in order to provide the desired flow rate for the cryofluid. The three orifices are staggered lengthwise about 0.7 to 0.9 in. apart from each other, with the distal-most orifice being spaced from about 0.34 in. to about 0.38 in. from the interior distal wall of the probe.

The singular continuous exhaust pathway for exit of the cryogenic fluid is optimized in order to achieve the desired flow rate of cryofluid exhaust which complements the embodiment of the supply orifices described above.

In an exemplary embodiment, the malleable end effector is made from a soft aluminum alloy and has a wall thickness of from about 0.020 in. to about 0.035 in., and an outside diameter of from about 0.16 in. to about 0.20 in.

In a further exemplary embodiment, the coiled spring is made from stainless steel, and has a pitch of from about 0.018 in. to about 0.022 in.

These features, as well as others, will become apparent with reference to the accompanying drawings and following description.

DESCRIPTION OF THE DRAWINGS

FIG. 3 is a cross-sectional view of the malleable end effector.

FIG. 4 is an enlarged cross-sectional view of the distal tip of the malleable end effector.

FIG. 5 is a cross-sectional view of an alternate configuration of the distal tip of the malleable end effector.

FIG. 6 is an enlarged cross-sectional view of the malleable end effector, showing the relative spacing of the orifices for the expansion of the cryofluid.

FIG. 7 is a cross-sectional view of the connection between the cryofluid supply tubes and the malleable end effector taken along line 7-7 in FIG. 3.

FIG. 8 is a cross-sectional view showing an alternate configuration of the connection between the cryofluid supply tubes and the cryofluid delivery tube.

FIG. 9 is a plan view of the cryofluid delivery and exhaust lines, and the coupling connecting such lines to the end effector.

FIG. 10 is a cross-sectional view of the coupling taken along line 10-10 in FIG. 9.

DESCRIPTION

The exemplary embodiments of the present disclosure are described and illustrated below to encompass cryogenic surgical instruments and, more particularly, to a cryogenic probe or cryoprobe for creating lines of ablation on cardiac tissue for the treatment of cardiac arrythmias such as atrial fibrillation. Of course, it will be apparent to those of ordinary skill in the art that the preferred embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure. Hereinafter, the exemplary embodiments of the present disclosure will be described in detail with reference to the drawings.

Figure 1:
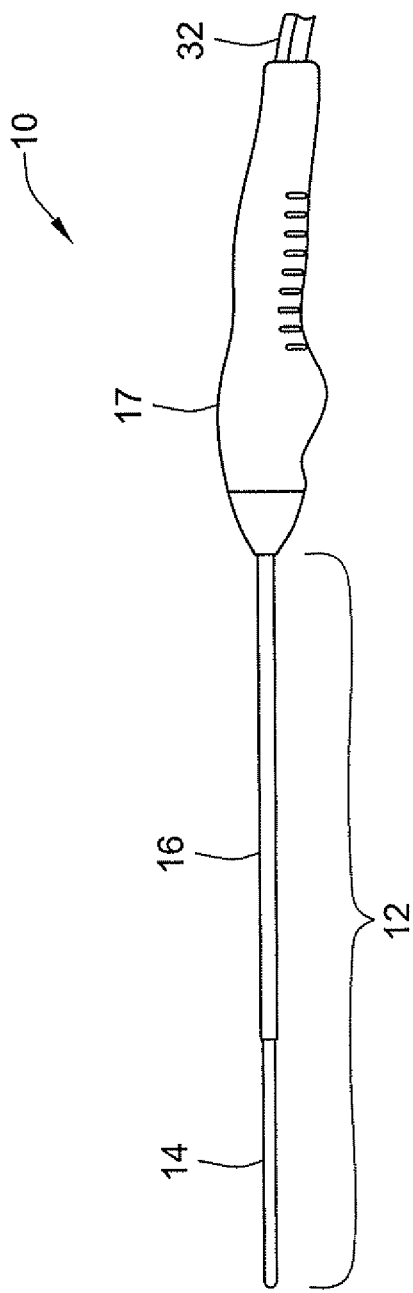
FIG. 1 is a plan view of the cryoprobe of the present disclosure showing the malleable end effector, the semi-rigid sleeve or shaft, the handle, and the flexible source/return tubing adapted to be connected to a console (not shown) for the supply and control of cryofluid.
Figure 2:
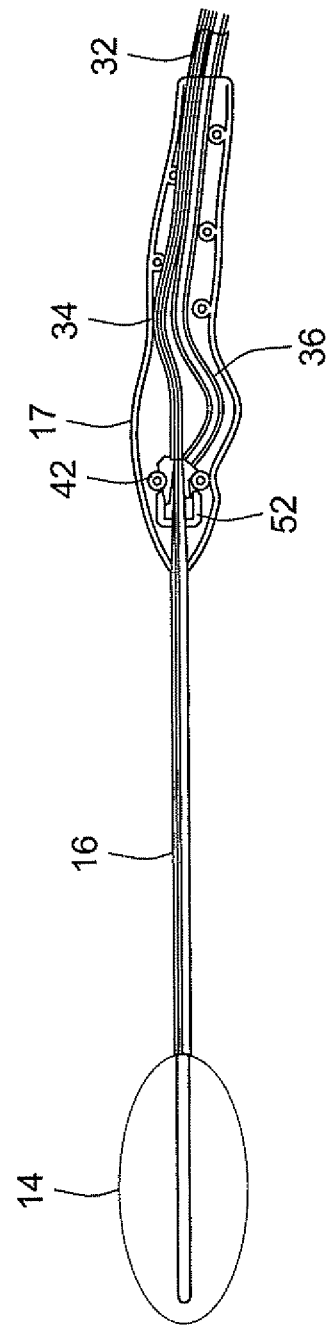
FIG. 2 is a vertical sectional view of the cryoprobe of FIG. 1 taken through the central line.

With reference to FIGS. 1 and 2, a first exemplary cryoprobe, generally designated 10, includes an elongated probe 12 that terminates in a malleable end effector 14. In use, the malleable end effector generates surface temperatures below −40° C. When the end effector 14 is applied to the tissue to be treated, freezing of tissue coming into direct contact with the probe results. Surrounding tissue is sequentially frozen by the withdrawal of heat from the tissue as the probe maintains contact with tissue over time.

The disclosed cryoprobe 10 may be used in an open procedure on an arrested heart, with the end effector 14 being applied to the endocardium or inner surface of the heart (through a purse-string opening), or alternatively to the epicardium or outer surface of the heart. The freezing of the cardiac tissue causes an inflammatory response (cryonecrosis) that blocks the conduction of electrical pulses.

More specifically, referring to FIGS. 1-5, the cryoprobe 10 comprises an elongated probe tube 15 whose distal portion comprises the malleable end effector 14. The tube has a smooth outer surface over its entire length. A semi-rigid sleeve 16, made of polycarbonate, overlies the proximal portion of the elongated probe tube, and both the tube and sleeve extend from and are secured to a handle 17. In this exemplary embodiment, the cryoprobe 10 has an overall length of approximately 43 cm, with the malleable end effector 14 having a variable length of up to approximately 10 cm, and the semi-rigid sleeve 16 and the handle 17 having a combined length of approximately 33 cm. If employed in a robotic device, the length of the probe tube may vary. All materials used in the cryoprobe 10 that are exposed to the cryofluid may be compatible with the cryofluid used in the device, and components intended for patient contact may be biocompatible. The device (and its packaging) may also be gamma stable, as gamma sterilization is an exemplary sterilization method.

The end effector/probe tube 15 is constructed of a relatively soft metal, such as Series 1000 aluminum alloy. Alternatively, gold, gold alloys, stainless steel, nitinol, or other malleable metallic alloys that have suitable thermal conductivity may be used. In exemplary form, the end effector 14 is malleable and formed into various shapes appropriate for making the different ablation lines, but is stiff enough for tissue conformance and to maintain its shape when applied to cardiac tissue without any secondary reinforcement. Likewise, the exemplary end effector is capable of being bent in an arcuate manner to have a minimum radius of approximately 0.5 in.

Figure 11:
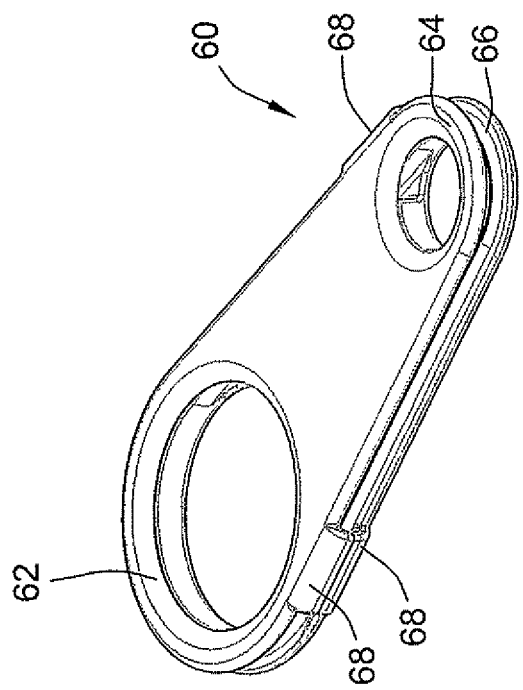
FIG. 11 is a perspective view of a bending tool that may be used in bending the malleable end effector of the cryoprobe into the desired shape.

A tool 60, such as that shown in FIG. 11, may be used for bending the end effector 14 into the desired shape. Alternatively, the end effector/probe tube 15 may be reshaped by hand. The tool 60 has ends 62, 64 that are curved in predetermined radii and a groove 66 extending about its edge for seating the end effector. The tip of the end effector may be secured in the groove 66 by arms 68 that overlie the groove.

The end effector 14 of the probe tube 15 is provided with internal flexible support walls to prevent kinking and to help maintain the circular cross-section of the end effector during deformation. In this exemplary embodiment, the end effector 14 is supported internally by a coiled spring 20 made of stainless steel. The spring 20 may also serve to capture segments of the end effector in the event that the end effector should fracture. The coiled spring 20 may be free-floating, or it may be retained in place on the interior of the end effector 14 by frictional engagement with the inner wall of the end effector, with at least a few coils of the spring being oversized to frictionally engage the inner wall of the end effector. In this exemplary embodiment, the spring 20 has a pitch of from about 0.018 in. to about 0.022 in. and an outside diameter of from about 0.115 in. to about 0.125 in.

The end effector 14 has a smooth exterior surface for contacting the tissue to be ablated. With reference to FIGS. 3 and 4, it is seen that the distal tip of the end effector 14 is closed and forms a blunt, atraumatic, generally hemispherical shape. This may be accomplished by limiting the opening in the end effector, by casting, spin forming, etc. As shown in FIG. 5, the blunt distal tip of the end effector may be formed by limiting the opening in the aluminum tubing 15, and closing the remaining opening with a separate plug 24 that may be formed of aluminum. The plug may be held in place by an epoxy 26 or other suitable adhesive. Alternatively, the plug 24 may be soldered, welded, press fit or cast into position.

All surfaces of the cryoprobe that are not intended for patient contact may be insulated for the protection of both non-target tissue and the user. To this end, the interior of the sleeve 16 creates an air pocket that serves to insulate the portion of the probe tube proximal of the end effector 14, thus protecting adjacent non-treated tissue from freezing tissue that may come into contact with the exposed portion of the sleeve 16. Similarly, the handle provides an insulated surface to hold the probe tube in position while manipulating the end effector.

Inside the end effector 14 a Joule-Thomson Effect is formed where the cryofluid undergoes expansion. The Joule-Thomson Effect is created by the expansion of gas that occurs as the cryofluid moves through the small orifice from each of the high pressure supply tubes into the low pressure expansion chamber comprised by the probe tube. Temperatures within the probe tube can fall below −60° C., and provide for surface temperatures of the end effector to reach less than −45° C., when nitrous oxide gas is used as the cryofluid.

In the illustrated embodiment, the end effector 14 houses a plurality of separate gas delivery passageways in the form of malleable supply tubes or hypotubes (not necessarily limited to three in number and made of stainless steel in this exemplary embodiment) designated 18a, 18b and 18c. Each of the supply tubes 18a, 18b, and 18c terminates in a reduced orifice 22a, 22b and 22c that forms a nozzle to deliver the gas into the expansion chamber (probe tube). Each nozzle has a cross-sectional area that achieves a flow rate of 600-630 ccm at 15 psi. In practice, this results in the individual orifices having an inside diameter of from about 0.003 to about 0.010 in. and a corresponding cross sectional area of from about 0.00000707 sq. in. to about 0.0000785 sq. in. The orifices are staggered lengthwise at 0.7 to 0.9 in. (2 cm) intervals. See Locations A, B and C, as shown in FIG. 6. The staggered multiple expansion nozzles allow for more uniform cooling over the length of the end effector 14.

The three cryofluid supply tubes 18a, 18b and 18c are connected at their proximal ends to a single cryofluid delivery tube 28. As shown in FIG. 7, the distal end of the cryofluid delivery tube 28 is triangular and the proximal ends of the three cryofluid supply tubes 18a, 18b and 18c are received therein and are secured to the delivery tube by, e.g., solder 30. Alternatively, as shown in FIG. 8, the distal end of the cryofluid delivery tube 28 may have a generally circular shape for receiving the proximal ends of the three cryofluid supply tubes.

The three cryofluid supply tubes terminate in the fluid expansion chamber (inside the probe tube), the internal diameter of which may be of sufficient cross sectional area to allow managed evacuation of the expanding cryofluids. The flow of the cryofluid through the probe tube and into the remaining exhaust tubing system may be controlled.

In this exemplary embodiment, the flow of cryofluid to and from the cryoprobe 10 is controlled from a separate console (not shown) that regulates and controls the pressure of the cryofluid introduced into the cryoprobe. Consequently, no valves or other similar gas flow controlling mechanisms are directly associated with the various components of the cryoprobe in this exemplary embodiment. The console is capable of pressurizing the probe for active defrost and provides for appropriate exhausting of expanded cryofluid. Alternatively, or in addition, hand controls associated with the handle 17 or foot switch controls may be provided.

In order to deliver cryofluid to the cryoprobe 10, a flexible tubeset 32 is provided that extends from the handle 17 and connects the probe tube to the console, the handle providing strain relief for the tubeset. The tubeset 32 comprises a high pressure (700 psi) delivery (inlet) line 34, preferably including a filter, that supplies cryofluid, such as nitrous oxide gas, to the cryoprobe and a low pressure (approximately 30 psi to 50 psi) return (exhaust) line 36 that evacuates the expanded cryofluid from the probe. The flexible delivery and return lines are capable of withstanding a minimum pressure of 1400 psi, with the delivery line having an inside diameter of 0.078 in., and the return line having an minimum inside diameter of 0.142 in. The tubeset 32 comprises a flexible tubing to facilitate user manipulation and has metal fittings 38 for connecting the delivery and return lines to the console. Differentiated end configuration and/or color coding for the delivery and return lines may be utilized in order to facilitate proper attachment to the console.

As best seen in FIGS. 9 and 10, a multipart coupling 40 connects the probe tube to the cryofluid delivery and return lines 34, 36. The coupling 40 comprises an gas exchanger fitting 42 that provides both a fluid pathway 44 between the proximal end of the delivery tube and the flexible delivery line, as well as a separate fluid 46 evacuation pathway between an interior chamber 48 for exhaust of expanded cryofluid from the probe tube and the flexible return line. The exchanger fitting 42, ferrule 50 and nut 52, may each be made from stainless steel, and are operative to secure the delivery/return lines and probe tube together.

In exemplary form, the cryoprobe may be configured to allow relative axial movement between the probe tube 15 and the semi-rigid sleeve 16 and handle 17, such that the end effector 14 may be retracted into the semi-rigid sleeve to protect it when not in use.

Figure 12:
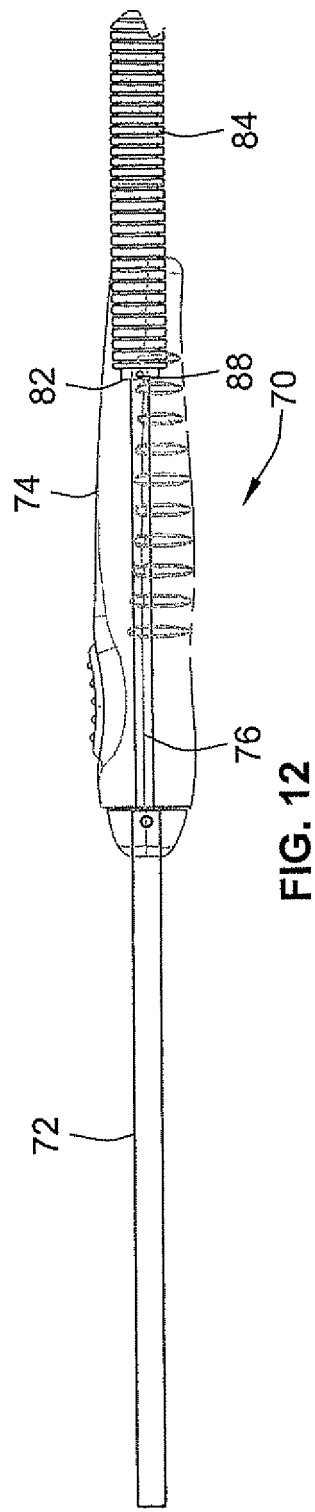
FIG. 12 is a view of a second embodiment of a cryoprobe having a retractable end effector, with the end effector being in the retracted position.
Figure 13:
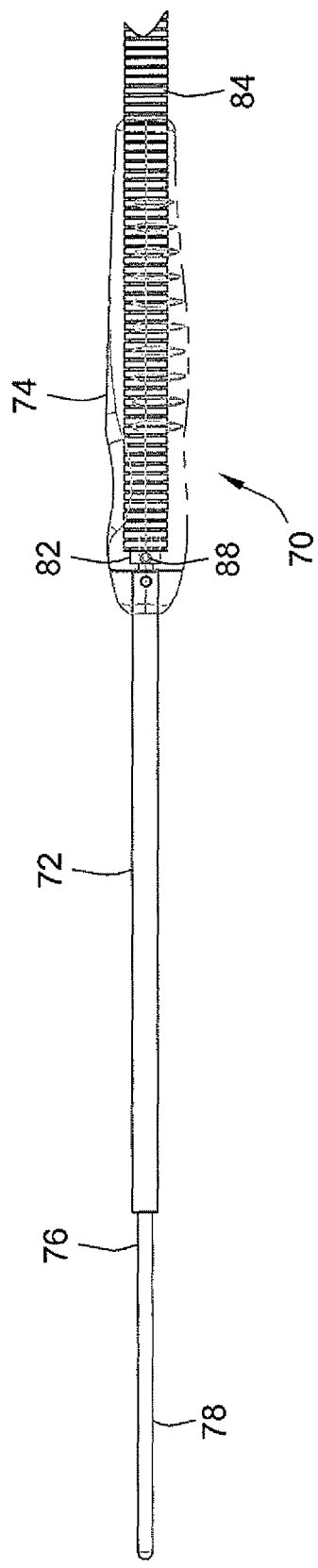
FIG. 13 is a plan view of the cryoprobe of FIG. 12 with the end effector in the extended position.
Figure 14:
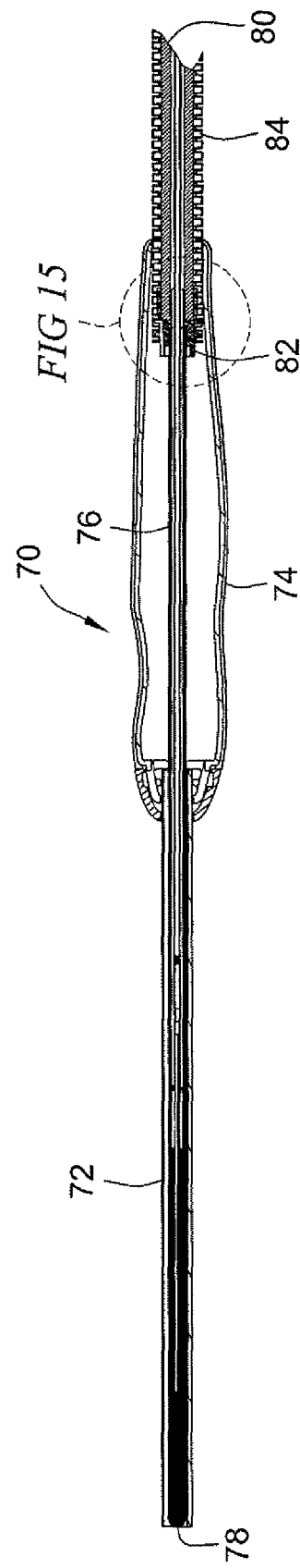
FIG. 14 is a cross-sectional view of the cryoprobe of FIG. 12, with the end effector in the retracted position.

As best seen in FIGS. 12 and 13, another exemplary cryoprobe 70 is shown having a semi-rigid sleeve 72 secured to the distal end of a handle 74, similar to that described above with respect to FIGS. 1 and 2. A probe tube 76 is engaged to track within the within the semi-rigid sleeve 72 so as to allow axial movement of the probe tube relative to both the semi-rigid sleeve and the handle. As such, the probe tube 76 is may translate lengthwise between an extended position, as shown in FIG. 13, in which the end effector 78 terminates beyond the distal end of the semi-rigid sleeve 72, and a retracted position, shown in FIG. 12, in which the end effector 78 terminates inside the semi-rigid sleeve when the proximal end of the probe tube 76 is located within the handle. Thus, the probe tube 76 may be retracted to protect the end effector portion of the tube during non-use, transit or storage and to achieve a more compact size to facilitate packaging, transit, and storage of the cryoprobe.

Turning to FIGS. 12-15, a coaxial cryofluid delivery/return tubing 80 is connected to the probe tube 76 by means of a collar 82 that is affixed to the proximal end of the probe tube 76. The delivery/return tubing 80 is provided with a corrugated tubing or jacket 84 that is secured to the collar 82 by means of barbs 86 on the collar (best seen in FIG. 15). The corrugated jacket 84 insulates the cryofluid delivery/return tubing 80 so that it is safe for the user to contact, thus allowing the user to extend or retract the probe tube 76 by holding the handle 74 in one hand and pushing or pulling on the corrugated jacket 84 with the other hand.

Figure 16:
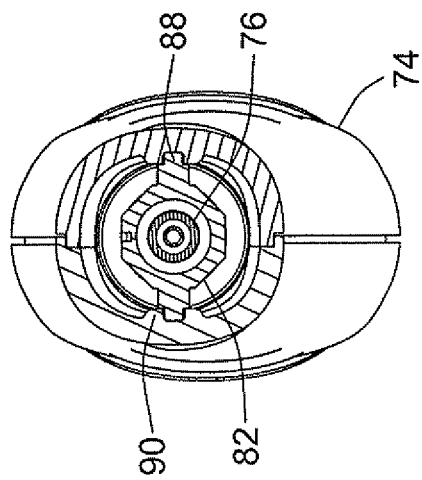
FIG. 16 is a cross-sectional view of the cryoprobe of FIG. 12 through the connection between the end effector and the cryofluid delivery/exhaust tubing.
Figure 15:
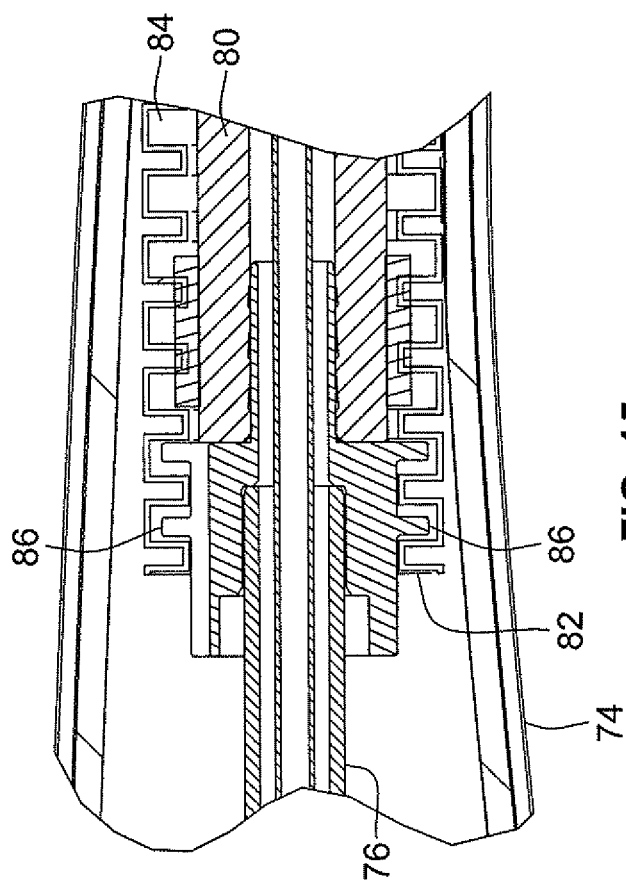
FIG. 15 is an enlarged cross-sectional view of the connection between the end effector and the cryofluid delivery/exhaust tubing.

In this exemplary embodiment, the probe tube 76 is provided with a guide feature that ensures that the probe tube 76 maintains alignment and orientation with the semi-rigid sleeve 72 and handle 74, and reduces the likelihood of the probe tube 76 binding up in the sleeve when moved between the extended and retracted positions. In the illustrated embodiment, this is accomplished by providing the collar 82 with a pair of opposed guide pins 88 (best seen in FIG. 16) that are received in elongated slots 90 formed on the interior of the handle 74.

Figure 17:
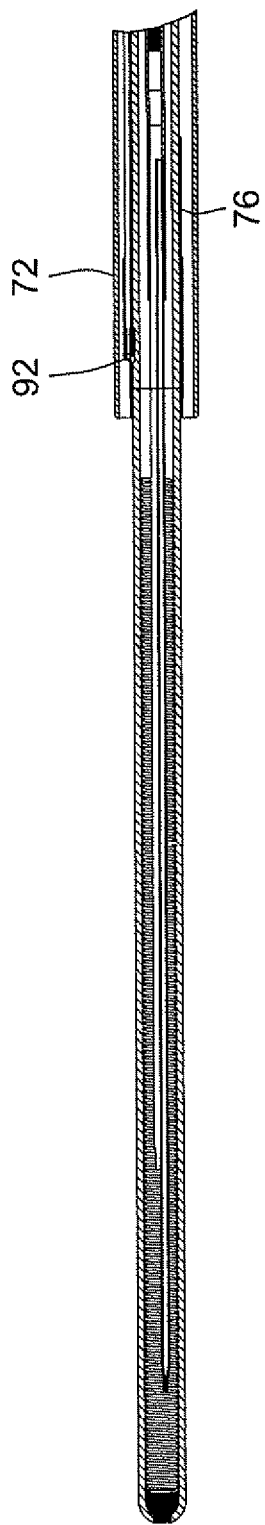
FIG. 17 is an enlarged cross-sectional view of the distal end of the semi-rigid sleeve and the exposed end effector.

In addition, the cryoprobe may be provided with a system for determining the surface temperature of the end effector and providing the user with that data. To this end, the outer surface of the probe tube may be provided with a temperature measuring device, such as a thermocouple 92, best seen in FIG. 17. The thermocouple 92 is preferably located on the probe tube 76 such that, when the probe tube is in the extended position, the thermocouple 92 remains within and is protected by the sleeve 72. Wiring on the outside of the probe tube transmits signals generated by the thermocouple 92 to a display (not shown) having a read-out visible to the user. The thermocouple may be a type T calibration thermocouple which is suitable ranging between −250° C. and 350° C.

Following from the above description and exemplary embodiments, it should be apparent to those of ordinary skill in the art that, while the foregoing constitute exemplary embodiments of the present disclosure, the disclosure is not necessarily limited to these precise embodiments and that changes may be made to these embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the disclosure discussed herein in order to fall within the scope of any claims, since the invention is defined by the claims and since inherent and/or unforeseen advantages of the present disclosure may exist even though they may not have been explicitly discussed herein.

What is claimed:

1. A cryogenic probe for ablating tissue comprising:
   a handle;
   an elongated probe metal tube extending from the handle having a proximal portion and a distal portion, the distal portion defining an end effector, the probe tube being closed at its distal end and having an interior surface and a smooth exterior surface;
   a semi-rigid insulative outer sleeve extending from a distal portion of the handle and overlying the proximal portion of the probe tube;
   a flexible support member supporting the interior surface of the distal portion of the probe tube; and
   a plurality of cryogenic fluid supply passageways disposed on the interior of the probe tube, each supply passageway having an outlet orifice, the outlet orifices being staggered along the length of the distal portion of the probe tube;

an insulated jacket operatively coupled to the elongated probe metal tube and extending from a proximal portion of the handle, the insulated jacket is repositionably mounted to the handle and configured to reposition the elongated probe metal tube when the insulated jacket is repositioned;

wherein the elongated probe metal tube is axially movable relative to the sleeve and the handle between a retracted position in which the end effector is inside the sleeve and an extended position in which the end effector is outside the sleeve.

2. The cryogenic probe of claim 1 wherein the elongated probe metal tube is fabricated from at least one of a Series 1000 aluminum alloy, gold, a gold alloy, stainless steel, and nitinol.

3. The cryogenic probe of claim 1 wherein the elongated probe metal tube has a wall thickness of from 0.020 in. to 0.035 in., and an outside diameter of from 0.16 in. to 0.20 in.

4. The cryogenic probe of claim 1 wherein the end effector has a length of up to 10 cm.

5. The cryogenic probe of claim 1 wherein the flexible support member comprises a coiled spring.

6. The cryogenic probe of claim 5 wherein the coiled spring has a pitch of from 0.018 in. to 0.022 in. and has an outside diameter of from 0.115 in. to 0.125 in.

7. The cryogenic probe of claim 1 wherein the number of cryogenic fluid supply passageways is three.

8. The cryogenic probe of claim 7 wherein the orifices of the cryogenic fluid supply passageways each have a cross-sectional area of from 0.00000707 sq. in. to 0.0000785 sq. in.

9. The cryogenic probe of claim 8 wherein each orifice is spaced apart 0.78 in. from an adjacent orifice, with the distal-most orifice being spaced from 0.34 in. to 0.38 in. from the interior distal wall of the elongated probe metal tube.

10. The cryogenic probe of claim 1 further comprising a thermocouple located on the surface of the elongated probe metal tube for providing a temperature measurement.

11. The cryogenic probe of claim 10 wherein the thermocouple is located on the surface of the probe tube such that it is within the insulative outer sleeve.

12. A cryogenic probe for ablating tissue comprising:
a cryogenic metal tube being closed at one end, the cryogenic metal tube including a deformable end effector having a wall thickness between 0.020 in. to 0.035 in., the deformable end effector at least partially housing a flexible support adjacent an interior wall of the deformable end effector, the deformable end effector and the flexible support at least partially circumscribing a cryogenic fluid supply line, the cryogenic fluid supply line including at least one nozzle;

an insulating sleeve repositionable with respect to the cryogenic metal tube and covering at least a portion of the cryogenic metal tube, the insulating sleeve having a sufficient length to cover the deformable end effector;

a handle mounted to a proximal portion of the insulating sleeve; and an insulated jacket coupled to the cryogenic metal tube and extending from a proximal portion of the handle, the insulated jacket is repositionably mounted to the handle and configured to reposition the cryogenic metal tube with respect to the insulating sleeve and handle.

13. The cryogenic probe of claim 12, wherein the cryogenic fluid supply line comprises a plurality of cryogenic fluid supply lines, with at least two of the plurality of cryogenic fluid supply lines each having a nozzle, where the nozzles are spaced apart from one another along a length of the deformable end effector.

14. The cryogenic probe of claim 12, wherein the deformable end effector is capable of being deformed to have a generally circular shape having a radius of approximately 0.5 inches.

15. The cryogenic probe of claim 12, wherein the flexible support comprises a helical coil.

16. A cryogenic probe for ablating tissue comprising:
a handle;
an elongated probe tube extending from the handle having a proximal portion and a distal portion, the distal portion defining an end effector, the elongated probe tube being closed at its distal end;

a semi-rigid insulative outer sleeve operatively coupled to and extending from a distal portion of the handle and circumscribing at least a portion of the probe tube;

a plurality of cryogenic fluid supply passageways disposed on the interior of the probe tube, each of the plurality of cryogenic fluid supply passageway having an outlet orifice, the outlet orifices being staggered along the length of the distal portion of the probe tube;

an insulated jacket operatively coupled to the elongated probe tube and extending from a proximal portion of the handle, the insulated jacket is repositionably mounted to the handle and configured to reposition the elongated probe metal tube when the insulated jacket is repositioned;

wherein the elongated probe tube is axially repositionable relative to the insulative outer sleeve and the handle between a retracted position in which the end effector is inside the sleeve and an extended position in which the end effector is outside the sleeve.

* * * * *